United States Patent
Amini et al.

(10) Patent No.: US 8,710,433 B2
(45) Date of Patent: Apr. 29, 2014

(54) PARTICLE-LOADED MEMBRANE FOR SOLID-PHASE-EXTRACTION AND METHOD FOR PERFORMING SALDI-MS ANALYSIS OF AN ANALYTE

(75) Inventors: Nahid Amini, Bromma (SE); Leopold L. Ilag, Stockholm (SE); Mohammadreza Shariatgorji, Solna (SE); Erik Gunnar Thorsén, Hägersten (SE)

(73) Assignees: Nahid Amini, Bromma (SE); Leopold L. Ilag, Stockholm (SE); Mohammadreza Shariatgorji, Solna (SE)

( * ) Notice: Subject to any disclaimer, the term of this patent is extended or adjusted under 35 U.S.C. 154(b) by 0 days.

(21) Appl. No.: 13/265,816

(22) PCT Filed: Apr. 23, 2010

(86) PCT No.: PCT/SE2010/050451
§ 371 (c)(1),
(2), (4) Date: Oct. 21, 2011

(87) PCT Pub. No.: WO2010/123452
PCT Pub. Date: Oct. 28, 2010

(65) Prior Publication Data
US 2012/0037798 A1    Feb. 16, 2012

(30) Foreign Application Priority Data
Apr. 24, 2009  (SE) .................................... 0950271

(51) Int. Cl.
*H01J 49/16*        (2006.01)

(52) U.S. Cl.
USPC ........................................ 250/288; 250/282

(58) Field of Classification Search
USPC .................................. 250/281, 282, 288, 289
See application file for complete search history.

(56) References Cited

U.S. PATENT DOCUMENTS

| | | | |
|---|---|---|---|
| 2002/0121595 A1* | 9/2002 | Sunner et al. | 250/281 |
| 2004/0226885 A1* | 11/2004 | Chen | 210/635 |
| 2005/0009120 A1* | 1/2005 | Mok et al. | 435/7.23 |
| 2006/0110295 A1 | 5/2006 | Wohleb | |
| 2007/0023627 A1* | 2/2007 | Finch et al. | 250/282 |
| 2008/0044893 A1* | 2/2008 | Pollack et al. | 435/305.3 |

OTHER PUBLICATIONS

Chen and Sun, "Determination of Trace Quarternary Ammonium Surfactants in Water by Combining Solid-Phase Extraction with Surface-Assisted Laser Desorption/Ionization Mass Spectrometry", Rapid Communications in Mass Spectrometry, 2001, 15, 2521-2525.*

Hennion, Marie-Claire., "Graphitized Carbons for Solid-Phase Extraction", Journal of Chromatography A, 885 (2000) 73-95.*

International Search Report and Written Opinion received for PCT Patent Application No. PCT/SE2010/050451, mailed on Jun. 4, 2010, 9 pages.

(Continued)

*Primary Examiner* — Robert Kim
*Assistant Examiner* — David E Smith
(74) *Attorney, Agent, or Firm* — Morrison & Foerster LLP

(57) ABSTRACT

A membrane comprising graphitized carbon black (GCB) with dual function for solid-phase extraction and surface-assisted laser desorption mass spectrometry (SPE/SALDI-MS) analysis is disclosed. Devices extraction comprising such membrane and methods utilizing such membranes are also disclosed.

16 Claims, 12 Drawing Sheets

(56) References Cited

OTHER PUBLICATIONS

International Preliminary Report on Patentability received for PCT Patent Application No. PCT/SE2010/050451, mailed on Nov. 3, 2011, 6 pages.

Amini et al., "SALDI-MS Signal Enhancement Using Oxidized Graphitized Carbon Black Nanoparticles", Journal of the American Society for Mass Spectrometry, vol. 20, 2009, pp. 1207-1213.

Chen et al., "Determination of Trace Quaternary Ammonium Surfactants in Water by Combining Solid-phase Extraction with Surface-assisted Laser Desorption/ionization Mass Spectrometry", Rapid Communications in Mass Spectrometry, vol. 15, 2001, pp. 2521-2525.

Hennion, Marie-Claire, "Graphitized Carbons for Solid-phase Extraction", Journal of Chromatography A, vol. 885, 2000, pp. 73-95.

Shariatgorji et al., "μ-Trap for the SALDI-MS Screening of Organic Compounds Prior to LC/MS Analysis", Anal. Chem., vol. 80, No. 14, Jul. 15, 2008, pp. 5515-5523.

Williams et al., "Liquid Chromatographic—mass Spectrometric Determination of the Metabolism and Disposition of the Antiretroviral Nucleoside Analogs Zidovudine and Lamivudine in C57BL/6N and B6C3F1 mice", Journal of Chromatography B, vol. 798, Issue 1, Dec. 5, 2003, pp. 55-62.

Amini, Nahid, "Novel Solid Phase Extraction and Mass Spectrometry Approaches to Multicomponent Analyses in Complex Matrices", Department of Analytical Chemistry, Doctoral Thesis, Jun. 2, 2010, pp. 1-62.

Shariatgorji, Mohammadreza, "Novel Clean-Up, Concentration and Laser Desorption/Ionization Strategies for Mass Spectrometry", Department of Analytical Chemistry, Doctoral Thesis, 2010, 131 pages.

* cited by examiner

PARTICLE-LOADED MEMBRANE FOR SOLID-PHASE-EXTRACTION AND METHOD FOR PERFORMING SALDI-MS ANALYSIS OF AN ANALYTE

CROSS REFERENCE TO RELATED APPLICATIONS

This is a U.S. National Phase patent application of PCT/SE2010/050451, filed Apr. 23, 2010, which claims priority to Swedish Patent Application No. 0950271-7, filed Apr. 24, 2009, each of which is hereby incorporated by reference in the present disclosure in its entirety.

BACKGROUND OF THE INVENTION

Matrix assisted laser desorption/ionization (MALDI), which provides the soft desorption/ionization of a wide range of analytes, has attracted the attention of scientists with different interests. The technique is suitable for desorption/ionization of molecules with different sizes and physical properties. Presently it is widely used for mass spectrometry of proteins, peptides, lipids, intact microorganisms, synthetic polymers and even small molecules. MALDI works based on desorption/ionization of analytes using laser irradiation. Commonly either a UV or an IR laser is used. The pulsed laser is focused on a sample spot causing desorption and ionization of the sample.

To obtain a MALDI-mass spectrum it is essential to co-crystallize the sample with a matrix. Matrices are usually organic acids with non-localized electrons that can absorb the laser energy and transfer it to the analyte of interest. The latter means that during this process both analyte and matrix ions will be generated. The matrix ions and clusters do not interfere with the high molecular weight analytes, however they are problematic with regard to analysis of small molecules (MW<500 Da). Matrix ions and clusters overlap with small molecule ions resulting in masking of the peaks corresponding to analytes of interest. To overcome this problem several techniques have been suggested to make laser desorption/ionization appropriate for analysis of small molecules such as drugs, pesticides and different groups of pollutants. For example, desorption/ionization on silicon surfaces and carbonaceous materials, which are media that can desorb/ionize small molecules without generating interferences in the low mass/charge (m/z) region. The technique is so called surface assisted laser desorption/ionization (SALDI). In addition these surfaces provide a simpler sample preparation procedure by eliminating the matrix addition step compared to the commonly used matrix assisted laser desorption mass spectrometry.

However the sensitivity of surface assisted laser desorption/ionization mass spectrometry (SALDI-MS) is relatively low and to be able to detect analytes appearing in low concentrations and dirty samples a pre-concentration/clean up step is necessary before analysis. Solid-phase extraction (SPE) is widely used for pre-concentration and clean up of samples. Graphitised carbon black (GCB) has previously been used as a solid-phase extraction media and it has been previously reported that it can also act as a surface for laser desorption/ionization of small molecules (Shariatgorji M, Amini N, Thorsen G, Crescenzi C, and Ilag L, µ-Trap for the SALDI-MS Screening of Organic Compounds Prior to LC/MS Analysis. *Anal. Chem.* 2008, 80, 5515-5523). In the above publication, GCB particles were placed in a small cartridge (µ-Trap) and used to solid-phase extract analytes. After sample extraction, GCB particles were removed from the cartridge using a capillary, placed on a steel plate and analysed by SALDI-MS, with the result that satisfactory MS-spectra could be obtained.

Large scale analysis of samples using SPE followed by liquid chromatography/mass spectrometry (LC/MS) has been performed in 96-well format (Williams L D, Von Tungeln L S, Beland F A and Doerge D R. Liquid chromatographic-mass spectrometric determination of the metabolism and disposition of the anti-retroviral nucleoside analogs zidovudine and lamivudine in C57BL/6N and B6C3F1 mice. *J Chromatogr B Analyt Technol Biomed Life Sci.* 2003 Dec. 5; 798(1):55-62. The known techniques have necessitated analysing each sample with the cumbersome LC/MS technique.

SUMMARY OF THE INVENTION

The present invention provides improved means and methods of performing solid-phase extraction of analytes and subsequent SALDI-MS analysis of the analytes.

One aspect of the invention relates to a particle loaded membrane, comprising a support and particles attached to the support, for solid-phase extraction of an organic analyte from a sample to be analysed, characterized by that:
  the particles comprise graphitized carbon black (GCB); and
  the support is suitable for surface-assisted laser desorption ionisation mass spectrometry (SALDI-MS) of analytes extracted on the particles.

In one embodiment, the particle loaded membrane is further characterized by that the support is essentially inert with regard to binding of the organic analyte. In another embodiment, the particle loaded membrane is further characterized by that the support comprises polytetrafluoroethylene (PTFE), cellulose, polyether sulfonate (PES), Nylon or glassfiber. In yet another embodiment, the particle loaded membrane is further characterized by that the support essentially consists of PTFE, cellulose, PES, Nylon or glassfiber. In a further embodiment, the particle loaded membrane is further characterized by that the support consists of PTFE, cellulose, PES, Nylon or glassfiber. In still another embodiment, the particle loaded membrane is further characterized by that the support consists of PTFE. In yet further embodiments, the particle loaded membrane is further characterized by that the support is about 0.01-5 mm, preferably about 0.5 mm in thickness. In yet further embodiments, the particle loaded membrane is further characterized by that the GCB particles have a size in the range of about 37.5-125 µm (120-400 mesh). In yet further embodiments, the particle loaded membrane is, further characterized by that the GCB content of the membrane is about 90% by weight. In yet further embodiments, the particle loaded membrane is further characterized by that the GCB particles are type 1 or type 4 GCB particles.

In a second aspect of the invention, a filter device suitable for solid phase extraction of an organic analyte from a sample by filtration is provided, characterized by that a membrane of the invention (see above) is arranged into the filter device such that the analyte is solid-phase extracted onto the membrane. An embodiment of the filter device is further characterized by that the device is a filter plate device. Another embodiment of the filter device is further characterized by that the device is a filter plate device having dimensions that conform to standards ANSI/SBS 1-2004, ANSI/SBS 2-2004, ANSI/SBS 3-2004 and/or ANSI/SBS 4-2004.

In a third aspect of the invention, a method of performing SALDI-MS-analysis of an organic analyte in a sample is provided, characterized by that it comprises the steps of:

performing solid phase extraction of the analyte onto a membrane or a device of the invention (see above); and performing SALDI-MS-analysis of the extracted analyte.

In one embodiment, the method of the invention is further characterized by that it further comprises the step of: iii) desorbing the analytes and performing quantitative liquid chromatography/mass spectrometry (LC/MS) on the analytes.

The improved means and methods of the invention provide at least the following benefits:
greater ease of use
better reproducibility
lower back pressures and/or better flow rates, which is especially important for analysis of voluminous samples
enabling the use of small-sized GCB particles providing better SPE performance
amenability for large scale analysis processes (especially automated processes) leading to reduced costs and improved speed of analysis
adsorbed samples can be readily stored and transported, providing amenability for decentralised sample processing, also leading to reduced costs
reduced consumption of solvents, which reduces the burden on the environment
toxic solvents are not required

DEFINITIONS

Figure 1:
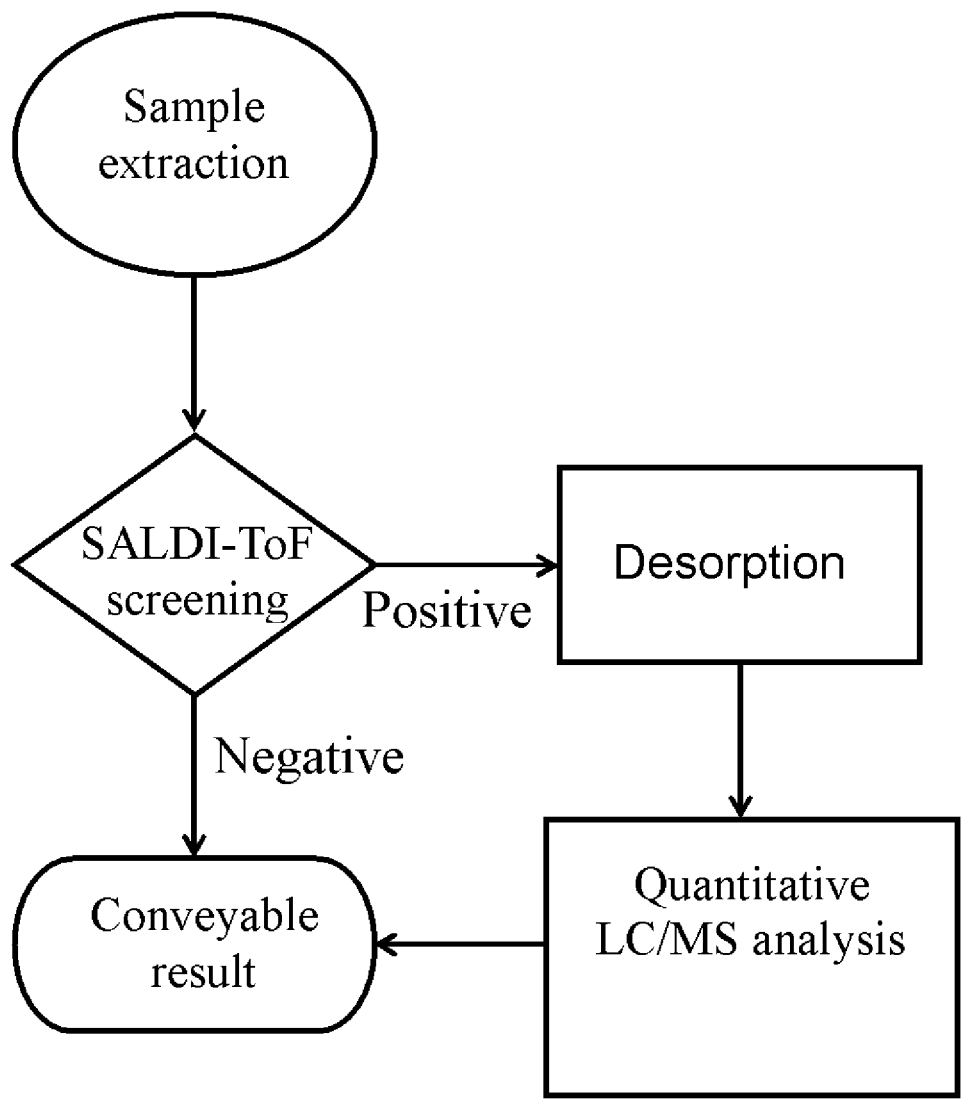
FIG. 1. Flow chart of the method of the invention using the membranes and/or devices of the invention.
Figure 2A:
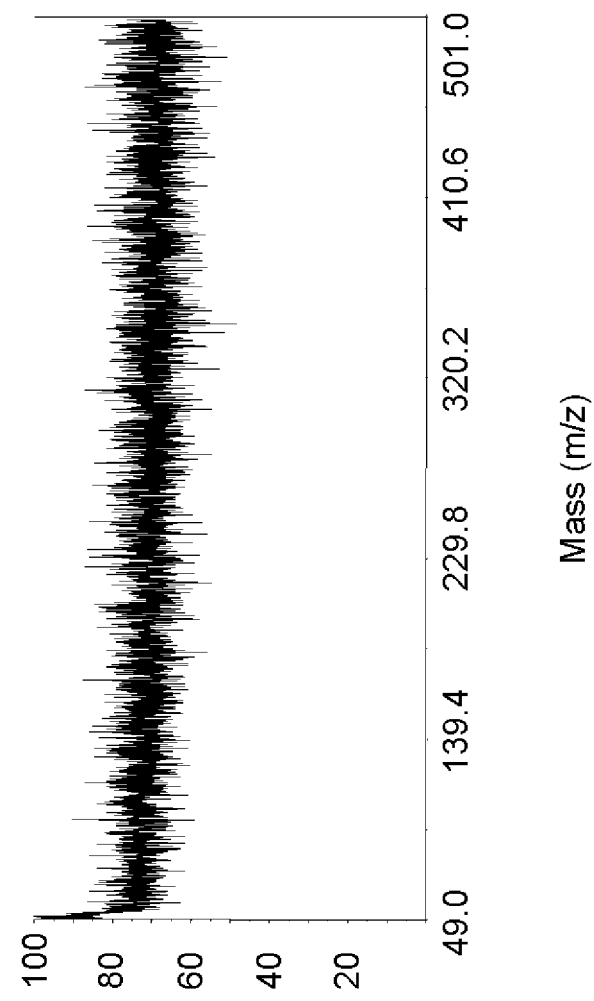
FIG. 2. Membrane material screening. Different candidate materials for a membrane of the invention were screened to evaluate interfering ions. a) PTFE; positive ion mode; b) Polyether sulfonate; positive ion mode; c) Nylon; positive ion mode. d) Mixed Cellulose; positive ion mode; e) Glass fiber; positive ion mode f) PTFE; negative ion mode; g) Mixed cellulose; negative ion mode.
Figure 2B:
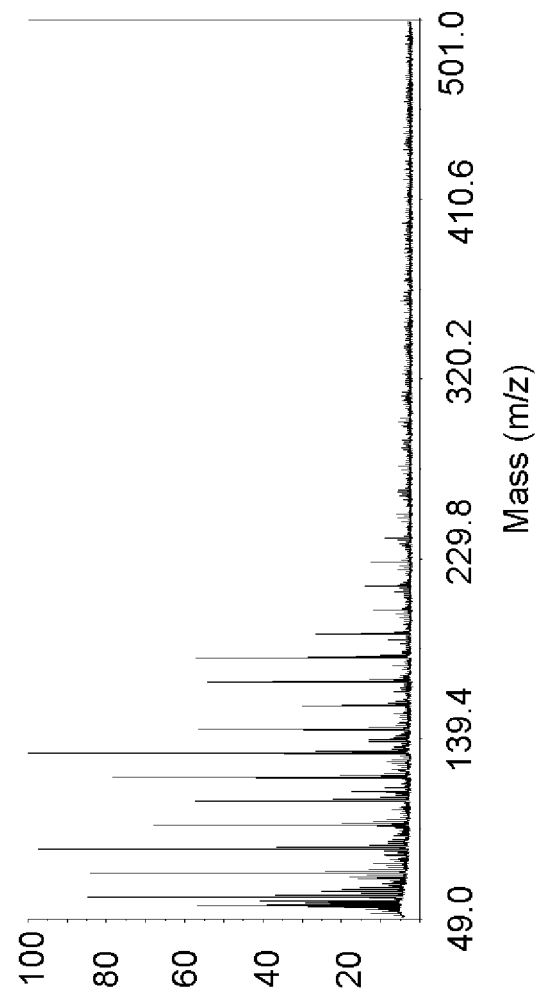
Figure 2C:
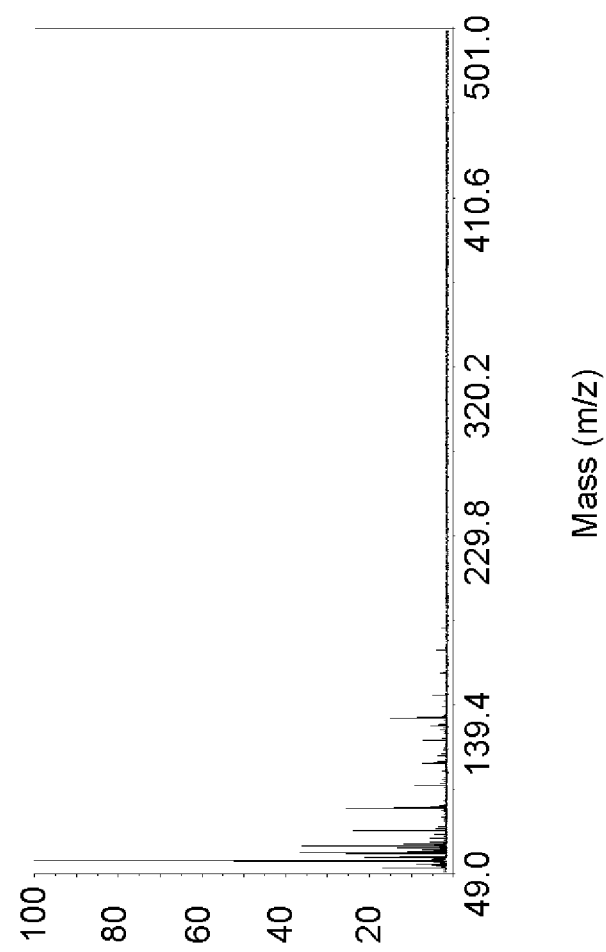
Figure 2D:
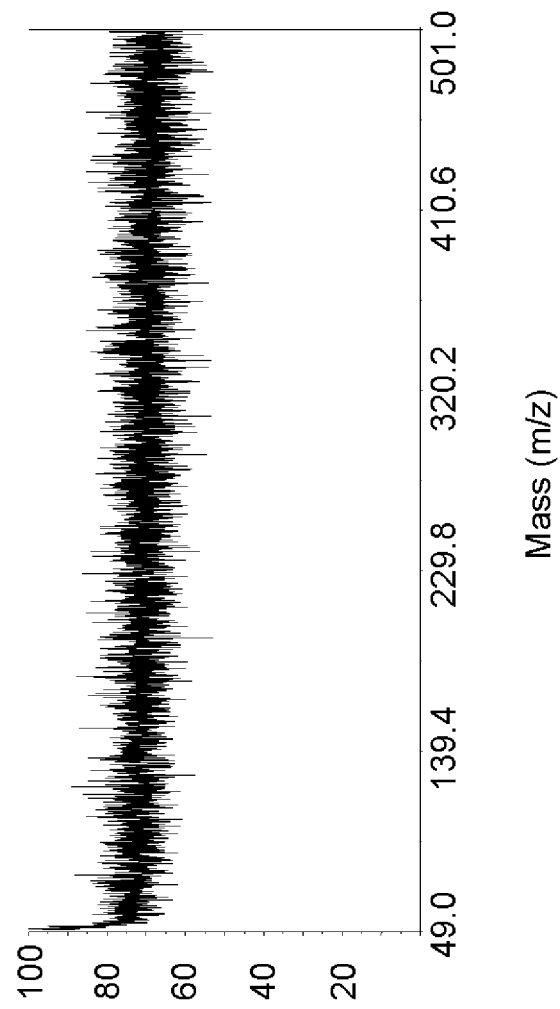
Figure 2E:
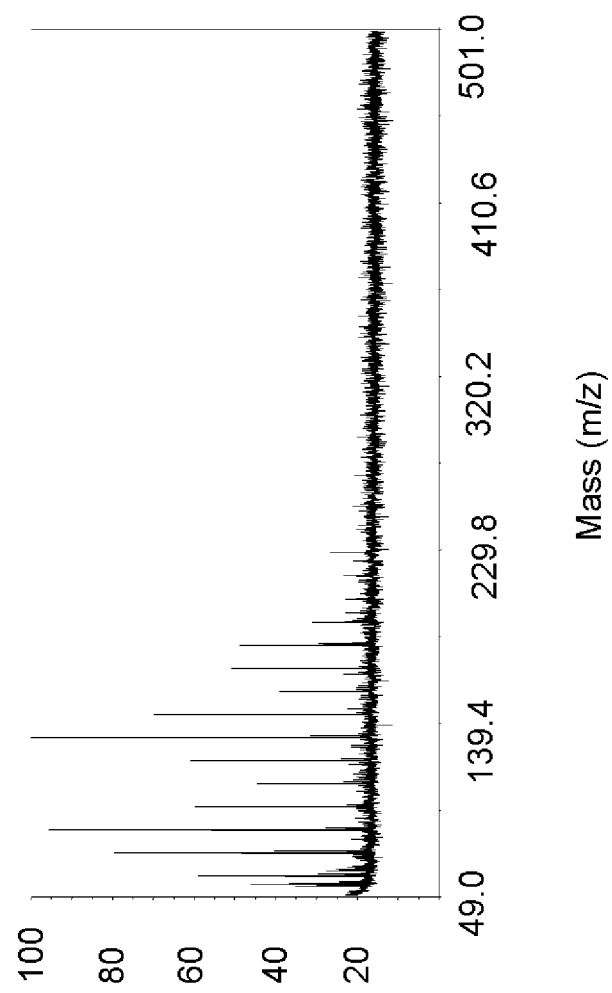
Figure 2F:
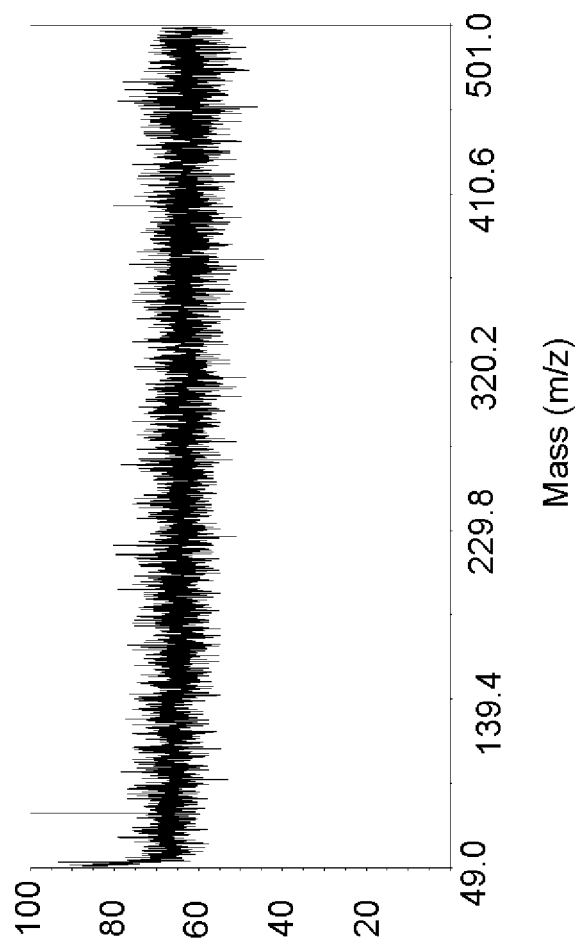
Figure 2G:
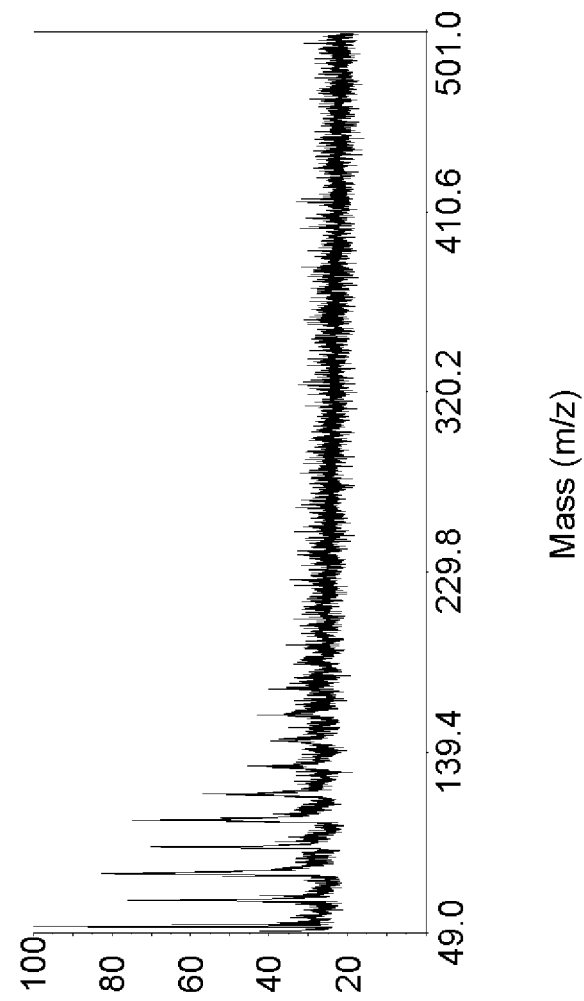

In the context of this disclosure, certain terms are defined according to the following. Terms not explicitly defined are to be understood to have their common meanings within the art.

Analyte means any chemical compound, which is of interest for analysis, including both quantitative and qualitative analysis. Examples of analytes include drugs, metabolites, toxins, pesticides, herbicides, pollutants and other compounds which may occur in for example biological samples, foodstuffs and environmental samples, such as water samples. For the purposes of the invention, the analytes are preferably organic or organometallic.

Carbon black is defined by International Carbon Black Association as virtually pure elemental carbon in the form of colloidal particles that are typically produced by incomplete combustion or thermal decomposition of gaseous or liquid hydrocarbons under controlled conditions, and has a Chemical Abstract Services number 1333-86-4. Its physical appearance is typically that of a black, finely divided pellet or powder. Carbon black is regarded as being chemically and physically distinct from soot and black carbon, with most types containing greater than 97% elemental carbon arranged as aciniform (grape-like cluster) particulate. On the contrary, typically less than 60% of the total particle mass of soot or black carbon is composed of carbon, depending on the source and characteristics of the particles (shape, size, and heterogeneity).

Graphitized carbon black (GCB) is carbon black heat-treated at a high temperature of about 2500-3000° C., most commonly about 2700° C., to induce a transformation in the molecular structure. A characteristic difference between GCB and graphite or carbon black is that GCB has a graphitic structure and oxygen containing groups at the edges. The graphitic structure of GCB facilitate $\pi$-$\pi$ interactions with analyte while the oxygen containing groups interact with analyte through ion exchange mechanisms. Thus, GCB has the potential of being a highly useful SPE media for a wide range of materials (through $\pi$-$\pi$ and ion exchange) while graphite and carbon black do not.

Solid phase extraction (SPE) is an extraction process that is used to extract certain compounds from a mixture of compounds. SPE uses the affinity of solutes dissolved or suspended in a liquid (known as the mobile phase) for a solid with which the sample is contacted (known as the stationary phase) to separate a desired compound(s). For the purposes of the invention, SPE is used to bind the analytes of interest to the stationary phase. The analytes of interest can then be removed from the stationary phase for collection in an additional step, in which the stationary phase is rinsed with an appropriate eluent.

SALDI-MS means surface assisted laser desorption/ionization mass spectrometry, and is characterised by that the laser desorption/ionization is achieved by utilising the characteristics of the surface onto which the analytes to be ionised are adsorbed. In contrast to matrix assisted laser desorption/ionization mass spectrometry (MALDI-MS), SALDI-MS does not utilise a matrix to absorb the laser energy and transfer it to the analyte of interest.

Cluster ions means interfering (undesired) ions produced by the SALDI-surface material or SALDI material supports or the MALDI matrix in conjunction with laser desorption/ionization of the analyte.

Membrane refers to a sheet of material, which is porous such that liquid may pass though it.

DETAILED DESCRIPTION OF THE INVENTION

It is known from prior art that GCB is a preferred material for acting both as SPE and SALDI-MS surface. In contrast to GCB, porous graphitic carbon, which is the only commercially available morph of graphite for SPE and chromatography does not work well as SALDI matrix (Shariatgorji et al., supra). Carbon black is not a good SPE sorbent since it interacts tightly with analytes resulting in a non-equilibrium sorption requiring carbon disulfide (toxic) as the solvent for elution. It also has a maximum tolerated laser intensity (MTLI), which is a drawback in SALDI-MS (Shariatgorji et al., supra). Thus, GCB is a preferred material having dual SPE/SALDI-MS functionality.

However, using the prior art methods for performing combined SPE/SALDI-MS, the GCB particles were packed in small cartridges that did not provide good flow rates for voluminous samples. For SALDI-MS analysis the GCB particles had to be removed from the cartridges by a capillary and placed on a stainless steel MALDI plate. This procedure resulted in analytical inaccuracy due to problems in picking a reproducible amount of the particles.

The cartridge format of the prior art technique also poses limitations to the particle size. Particles that are smaller provide better SPE performance but increase back-pressure and limit the flow rate in the cartridge and vice versa.

The manipulations involved in the prior art techniques are not easily automated, thus the prior art technique is not well suited for large-scale analysis of multiple samples.

In their efforts to solve the problems associated with handling GCB particles, the inventors realised that it could be advantageous to attach the particles to a solid membraneous support, if a compatible support could be devised. The sample could be passed though the membrane, solid-phase extracting analytes to the GCB particles. The membrane format would also allow the use of small-sized GCB particles without increasing the back pressure or compromising the flow rate. The membrane could then be placed in a SALDI-MS instrument and the sample ionised directly from the GCB particles.

Particle-Loaded Membrane

In addition to arriving to the realisation that it is advantageous to attach the particles to a solid membraneous support, a suitable solid support needed to be devised. It was realised that the solid support would need to have certain performance characteristics in order to be suitable for a combined SPE/SALDI-MS-procedure. Preferably the support should be inert with regard to analyte binding. Naturally, the binding characteristics vary between analytes and also depend on other conditions such as solvents and temperatures, but generally as little binding to the support as possible is preferred, so that as much analyte as possible binds to the GCB particles, where they are available for SALDI-MS-analysis. The support should also tolerate the solvents used, without degrading or swelling excessively. The support should also have good flow characteristics and the flow should not be easily clogged by dirty samples. The support material should have sufficient mechanical strength. Most importantly, the support must not produce interfering cluster ions in conjunction with laser desorption of the sample. For small molecule analysis m/z values of below 500 (that is, ions of 0-500 Da/charge) are of interest and as soon as cluster ions appear in this range they interfere with the spectrum of interest.

In example 1, the inventors tested a number of known filter membrane materials for their propensity for producing cluster ions. In positive ionisation mode, it was found that PTFE and cellulose had the best properties in this respect, followed by (in the order of preference) nylon, glass fiber and polyether sulfonate (PES). The best performers in positive ionisation mode were tested in negative ionisation mode and it was found that PTFE produced less cluster ions than cellulose. Therefore, the most advantageous solid support material with respect to cluster ionisation was found to be PTFE. Any of the other materials could also be used but the maximum usable laser intensity is lower with these materials, which impairs the analytical performance of the SALDI-MS.

Cellulose has the potential disadvantage of having a tendency to swell when used with aqueous samples. PTFE has good properties with regard to chemical resistance and is relatively inert. PTFE also has good mechanical strength.

The inventors proceeded by having a GCB-loaded PTFE membrane produced (see example 2). The PTFE-GCB membrane was shown to facilitate a rapid set up for solid phase extraction while its flat surface provides fast and easy matrixless SALDI-MS analysis. It was shown that the sample flow, membrane stability (chemical and mechanical), analyte binding, and analytical performance of a PTFE-GCB-membrane were suitable for SPE/SALDI-MS analysis of organic analytes from dilute samples.

Other support materials than specified here can be used in the membrane of the invention, as long as the support is suitable for comprising GCB particles and suitable for the SPE/SALDI-MS dual application with regard to the above criteria of sufficient inertness, chemical and mechanical stability, flow characteristics and interfering cluster ion formation.

All of the tested support materials can be used as the sole material, mixed with each other or mixed with other materials having suitable properties.

The support material of the invention preferably comprises PTFE, cellulose, nylon, glass fibre or polyether sulfonate. More preferably, the support essentially consists of PTFE, cellulose, nylon, glass fibre or polyether sulfonate. Even more preferably, the support consists of PTFE, cellulose, nylon, glass fibre or polyether sulfonate. Most preferably, the support consists of PTFE.

Preferably, the membrane should be 0.01-5 mm thick, more preferably 0.05-3 mm, even more preferably 0.1-2 mm and most preferably about 0.5 mm. The thickness of the membrane is a trade-off between flow rate, binding capacity and mechanical strength. A thicker membrane results in reduced flow rate (given constant pressure), higher binding capacity and higher mechanical strength, whereas a thinner membrane results in the opposite. Higher pressures may be used with thicker membranes to force the sample through with reasonable speed.

Different types of GCB vary in their surface area and it is known from prior art that essentially any of them can be used for SPE/SALDI-MS. Preferably, the GCB particles are of type 1 or type 4. Ideally, the surface area of the particles should be large in relation to weight. Larger area provides more binding capacity for analytes. The inventors have shown good function using GCB particles having a surface area of 210 $m^2/g$, but GCB variants of both lower and higher surface area are known in the art. Preferably, the surface area ($m^2/g$) of the GCB particles is from about 10 to 1000, more preferably 50-700, even more preferably 100-500, yet more preferably 150-300, and most preferably about 210.

Typically the GCB particles have to be more than 125 μm (400 mesh) for prior art cartridge or column applications to provide reasonable flow rates and back pressures. However, smaller particles typically provide better SPE performance than large particles due to their larger surface area-to-volume ratio. Incorporating the GCB particles into a membrane of the invention allows the use of smaller than 400 mesh particles with reasonable flow rates and back pressures. Thus, in one preferable embodiment, the GCB particles of a membrane of the invention have a size in the range of 37.5-125 μm (120-400 mesh).

Optionally, the surface of the GCB particles could be chemically modified and/or derivatised to improve SPE properties and/or SALDI characteristics of the surface. Surface oxidation could be a starting point for addition of functional groups to the surface of GCB. Carboxylic acid groups formed on the surface of GCB are a good starting point to create different functional groups such as metal chelate groups, fluorine containing groups, amino groups and affinity groups.

The GCB-membrane is preferably conditioned prior to SPE to reduce the quinone groups present on the surface of the GCB particles to less reactive hydroquinones. This can be achieved e.g. by passing though the membrane 8 volumes of $CH_2Cl_2$/MeOH 80/20, 2 volumes of MeOH followed by volumes of acetic acid 1% and finally 2 volumes of ascorbic acid (10 g/L), wherein the quantity of one volume is adjusted according to the size of the membrane.

The GCB content of the membrane can be varied. The content should be sufficient to provide sufficient analyte binding capacity, depending on the type of the analyte, the sensitivity of the MS-instrumentation, and the sensitivity required. Preferably, the content should be as high as the support material is able to support. The GCB content may lie in an interval between from 1% and up to 99% by weight of the membrane, the limits of the interval included. The GCB content (by weight) may also lie within any interval established with the above stated figures the limits of such an interval being included. The GCB content (by weight) is at least 1%, preferably at least 30%, more preferably at least 50%, even more preferably at least 70% and still more preferably at least 90%. The most preferable GCB content of the membrane is about 90% by weight.

Devices Comprising a Particle-Loaded Membrane of the Invention

A membrane of the invention (see above) may be used with various filter devices known from the prior art. A device may be a single filter holding device, such as the one used in Example 2. For rapid analysis of multiple samples, a membrane of the invention may preferably be used in a filter device for multiple samples, preferably a filter plate device. Filter plate devices and their uses are well known. Typically, a filter membrane is arranged to the bottom of a multi-well plate having standard outer dimensions and a standard well dimensions/layout (e.g. a 96-well plate). When used, the samples to be filtered or extracted are placed (e.g. pipetted or injected) into the wells. Then, either positive or negative pressure is usually applied to force the samples though the filter, onto which analytes may bind, depending on the properties of the filter material and the analyte.

Figure 4A:
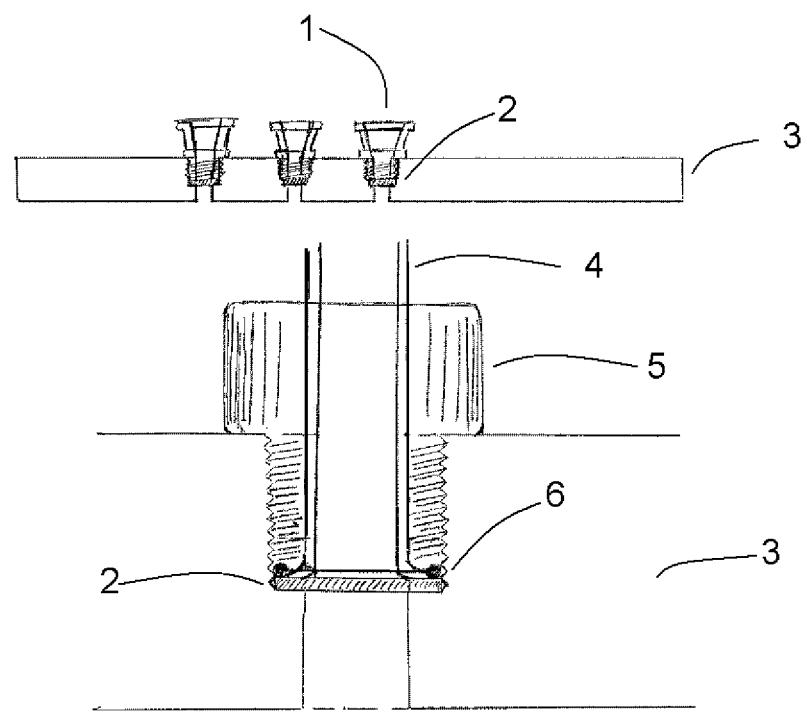
FIG. 4. Illustration of an exemplary filter plate device of the invention. a) Cross-sectional side view of a filter plate device utilising a single piece of a membrane of the invention for multiple samples (top: before assembling; bottom: device assembled for use). b) Perspective illustration of the assembly of the device and its connection to a vacuum manifold. c) Illustration of a device comprising Luer-type couplings in multiple through-holes that comprise individual pieces of a membrane of the invention. Designations for components: luer type coupling (1), membrane piece (circular shown) (2), Block of poly(methyl methacrylate) (PMMA) or similar suitable material with through-holes and threading (3), tubing (shown with flanges at end) (4), flat-bottom fitting (5), O-ring (6), vacuum chamber (7), thread for fitting (8), through-holes (9), groove for tight fitting onto vacuum chamber (10).
Figure 4B:
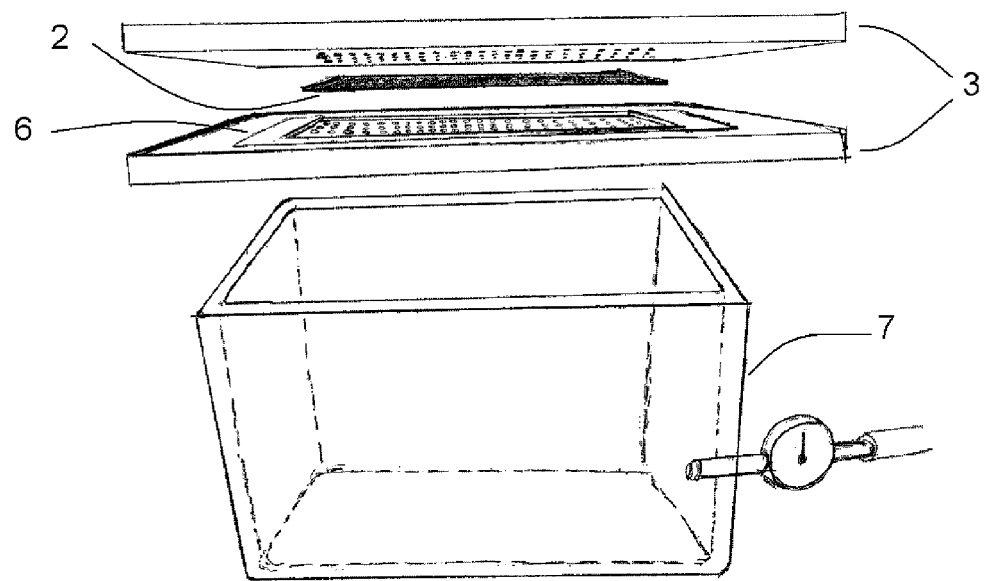
Figure 4C:
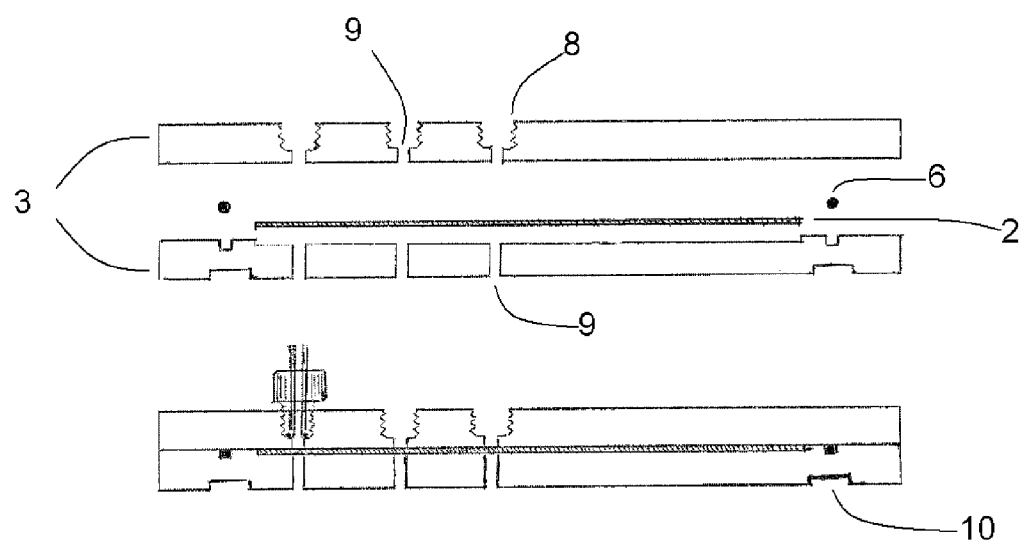

Filter plate devices of the invention are illustrated in FIGS. 4a-c. A filter device for simultaneous absorption of multiple samples may be arranged such that multiple samples are absorbed on different locations on a single piece of a membrane (see e.g. FIG. 4a). Alternatively, a filter device for simultaneous absorption of multiple samples may comprise individual pieces of the membrane for each sample (see e.g. FIG. 4c).

Thus, in one aspect of the invention, a filter device is provided wherein a membrane of the invention is arranged into the filter device such that the analyte is solid-phase extracted onto the GCB particles of the membrane when the sample is filtered with the device. For use with multiple samples, the filter device is preferably a filter plate device. The filter plate device preferably has standard dimensions and layout such that it may be used with existing filtering devices. Preferably, the plate device has dimensions conforming to the standards of the Society for Biomolecular Screening ANSI/SBS 1-2004, ANSI/SBS 2-2004, ANSI/SBS 3-2004 and/or ANSI/SBS 4-2004.

One advantage of using filter plate devices is that it simplifies automation of analysis of large numbers of samples. Handling of standardized plates is readily automated and many different solutions for the handling are commercially available.

Since many if not most analytes of interest (such as pesticides) are stable when bound to GCB, it is also possible to perform the SPE in a different place and at a different time from the SALDI-MS (and the optional quantitative, e.g. LC/MS) analysis. A laboratory with simple equipment (only a filtration apparatus is needed) can reproducibly process samples using a filter device (preferably a filter plate device) of the invention. The device having the analytes bound to it may then be shipped to a laboratory having more advanced instrumentation (such as SALDI-MS and LC/MS) and possibly a high level of automation, for later analysis. It may also be advantageous to accumulate and store samples before initiating a quantitative analysis run even when such instrumentation is readily available, e.g. from cost-efficiency point of view. To summarise, the filter devices of the invention provide more efficient use of advanced instrumentation, leading to savings in the analysis cost per sample.

Novel Methods of Analysis

Since SALDI-MS analysis only consumes very small amounts of analyte from the surface of the membrane, it is possible to non-destructively screen samples adsorbed on membranes with SALDI-MS for presence of analytes of interest. This screening makes it possible to select the samples that are worthwhile to analyse by quantitative methods, e.g. LC/MS analysis, which is a more sensitive and quantitative than SALDI-MS, but also more expensive and cumbersome.

Preferably, the membrane(s) (or portions of a membrane) that have been screened positive with SALDI-MS, still containing the majority of the analyte(s) is/are eluted for further quantitative analysis, e.g. by LC/MS analysis. The elution can be done for example by using a suitable solvent such as methanol or $CH_2Cl_2$/methanol (80/20) containing 50 mM TFA.

The eluted sample may be used directly for e.g. LC/MS provided that the solvent is compatible with the downstream analytical method. If necessary, the solvent may be evaporated and the sample redissolved in a suitable solvent prior to further analytical, e.g. LC/MS analysis. For example, 1 mL of the eluting solvent is passed through the membrane at the flow rate of 1 μl/min. The eluted solution collected in a glass vial is evaporated by a stream of nitrogen and the eluted solutes are dissolved in a solvent which is compatible with LC/MS.

Briefly, according to the flow chart of FIG. 1, all samples are individually passed through a membrane of the invention, or a specified portion of a single membrane (preferably using a filter plate device of the invention), after which said membrane is placed in a laser desorption/ionization mass spectrometer to collect the SALDI-MS spectrum of each sample. Negative samples can be excluded from further time/cost consuming quantitative analysis e.g. LC/MS. Optionally, positive samples are eluted from the membrane and subjected to quantitative analysis, e.g. LC/MS.

The dual functionality of the GCB membrane of the invention (SPE and SALDI-MS) and the outlined strategy efficiently decrease the number of the samples to be analyzed by a more cumbersome quantitative analytical method e.g. LC/MS, and thereby provides faster and more cost-efficient analysis of multiple samples. The solvent consumption is also reduced, lessening the environmental impact of the analysis.

The details and particulars described above and in the claims and relating to the different aspects of the invention such as methods, membranes and devices apply mutatis mutandis to the other aspects of the invention.

While the invention has been described in relation to certain disclosed embodiments, the skilled person may foresee other embodiments, variations, or combinations which are not specifically mentioned but are nonetheless within the scope of the appended claims.

All references cited herein are hereby incorporated by reference in their entirety.

The expression "comprising" as used herein should be understood to include, but not be limited to, the stated items.

The invention will now be described by way of the following non-limiting examples.

EXAMPLES

Example 1

Screening of Support Materials

Various potential support materials were screened for their suitability for the dual SPE/SALDI-MS application. Materials known to be suitable for filter membranes, were tested for their propensity to produce cluster ions in conditions relevant to SALDI-MS. Membranes consisting of polytetrafluoroethylene (PTFE), mixed cellulose, nylon, glass fiber and polyether sulfonate were tested. The membranes were obtained commercially from Millipore, except for nylon which was from Supelco.

SALDI mass spectra were obtained using a Voyager DE-STR time-of-flight mass spectrometer (Applied Biosystems), in reflector mode. A pulsed 337 nm nitrogen laser was used for desorption. The acceleration voltage was set to 20 kV, the delay time to 150 ns, and the grid voltage to 65%. All mass spectra were accumulated from five different spots, 20 shots per spot, and the resulting 100 spectra were averaged.

The spectra shown in FIG. 2a-g were taken at laser intensity of 2700 in the positive ionization mode. For small molecule analysis m/z values of below 500 are of interest and as soon as cluster ions appear they interfere with the spectrum of interest. In positive ionisation mode both PTFE and cellulose gave excellent results.

In negative ionization mode (FIGS. 2f-h) cellulose gives clusters at a lower laser energy compared to PTFE, as shown in the spectra.

Example 2

Proof-of-Concept Using a GCB-Loaded PTFE Membrane to Screen Positive Samples Using SALDI-MS Prior to LC/MS Analysis Chemicals and Reagents Methanol was purchased from BDH (Poole, England). Acetonitrile, dichloromethane, ascorbic acid and acetic acid were obtained from Merck (Darmstadt, Germany) and formic acid from Riedel-de Haën (Seelze, Germany). Trifluoroacetic acid, methomyl, chloridazon, cyanazine, carbofuran, metsulfuron-methyl, simazine, metazachlor, metalaxyl, atrazine, sebuthylazine, propazine, parathion-methyl, malathion, azinphos-ethyl, metolachlor, diazinon and atrazine-desethyl-2-hydroxy were purchased from Sigma-Aldrich (Milwaukee, Wis., USA). Water was purified by a Millipore water purification system and had a resistance >18 MΩ/cm.

Membrane Set-Up and SPE Procedure

The graphitized carbon black (GCB) membrane was manufactured using GCB 4 particles (mesh >400, surface area 210 m$^2$/g; kindly provided by the Laboratori Analitici di Ricerca Associati, Rome, Italy), as a sheet on request by 3M (USA) based on 3M™ Empore™ Extraction Disk technology. It was cut into 13 mm diameter pieces and placed into Swinnex® filter holders (Millipore) in between two Swinnex® gaskets (Millipore). The filter holders were then mounted on a SPE vacuum manifold (VacMaster-10, Biotage). The amount of GCB present on each membrane was approximately 23 mg. Conditioning of the membrane was initiated by passing 8 mL of CH$_2$Cl$_2$/MeOH 80/20, 2 mL of MeOH followed by 10 mL of acetic acid 1% and finally 2 mL of ascorbic acid (10 g/L) to reduce the quinone groups present on the surface to less reactive hydroquinones.

A solution of fifteen pesticides in water at a concentration of 0.1 μg/mL was used to evaluate the retention behavior as well as the desorption ability from the membrane. A 1 mL solution was passed through the membrane at a flow rate of approximately 2 mL/min (five replicates) after conditioning the membrane as stated above. The eluates from each membrane were collected to determine the breakthrough values.

After drying the membrane with a stream of nitrogen for about 15 minutes, 1 mL of MeOH and 2 mL of CH$_2$Cl$_2$/MeOH 80/20 containing 50 mM TFA were used for desorption of analytes. The extracts were collected in Champaign shaped vials (Agilent technologies). A gentle stream of nitrogen was used to assist evaporation of the solvent from the eluent, which was stopped before they were completely dry. The extracts were dissolved in 0.2 mL of MeOH/H$_2$O 40/60, shaken and analyzed immediately using LC/MS.

To explore variations in the recoveries caused by performing SALDI analysis, the membrane, sandwiched in between two gaskets, was transferred onto a stainless steel plate after passing the sample through it. The plate was modified in-house so that the depth of the membrane plus the gaskets did not exceed the depth of the original plate, when placed on it. After LDI was performed, the membrane was put back into the holder and the remaining analytes were desorbed.

To study the effect of different flow rates on the amount of breakthrough of pesticides from the membrane, a 5 ng/mL solution of pesticides in water was prepared and 20 mL of it was passed through each membrane at five different flow rates of 7-10, 15-19, 26-30, 35-40 and 46-50 mL/min with five replicates for each experiment.

Samples having volumes of, 100, 250, 500, 750 and 1000 mL, and concentrations of 1.00, 0.40, 0.20, 0.13 and 0.10 ng/mL respectively were passed through membranes at a flow rate of 30 mL/min in five replicates. The eluates were collected and 500 μL of each was injected manually in the LC/MS/MS.

To investigate retention capacity of the membrane, five solutions of pesticides having the following concentrations: 1, 5, 10, 25 and 30 μg/mL were prepared. Each solution was passed through five membranes at a flow rate of 2 mL/min and the breakthrough samples were collected for further analysis.

SALDI Analysis

All SALDI mass spectra were obtained using a Voyager DE-STR time of flight mass spectrometer (Applied Biosystems), in reflector mode. A pulsed 337 nm nitrogen laser was used for desorption. The acceleration voltage was set to 20 kV, the delay time to 150 ns and the grid voltage to 65%. All mass spectra were accumulated from five different spots, 20 shots per spot, and the resulting 100 spectra were averaged.

LC/MS/MS Analysis

For LC/MS/MS a binary liquid chromatography system (Shimadzu, Japan) consisting of two pumps (LC-10 ADvp), a degasser (DGU-14 A), a system controller (SCL-10 Avp) and an auto injector (SIL-10 ADvp) was coupled to a triple quadrupole API 2000 (Applied Biosystems/MDS Sciex, Canada) mass spectrometer.

Pesticides were separated on a C-18 HPLC column (Alltima, 250 mm×4.6 mm i.d., 5 particles; Alltech). The mobile phases used consisted of water (A) and methanol (B), both containing 1 mM of formic acid; a 30-min linear gradient from 50% B to 85% B. The flow rate was set to 1.0 mL/min, 0.2 mL/min of which was directed towards the mass spectrometer and the rest to waste. The retention times for all of the compounds are listed in Table 1.

The analytes were ionized by +ESI under the following operating parameters: curtain gas 30 psi; collision gas 6 psi; ion spray voltage 4500 V; temperature 450° C.; ion source gases 1 and 2, 30 and 40 psi, respectively. To select fragments with the highest signal/noise ratios for each parent ion, the collision energy was ramped from 5 V to 60 V in intervals of 5 V. Details of the MRM transitions, including the optimum collision energies, declustering potentials and focusing potentials, are listed in Table 1.

Agricultural Water Analysis

Agricultural water originating from rice fields was collected from Babolsar, a city situated in the Northern part of Iran by the Caspian Sea and stored at 4° C. until used. 900 mL of the water was filtered though glass fibre prefilters (pore size of 1.2 µm, Millipore) prior to being passed through the GCB membrane. The membrane was first screened by SALDI/MS followed by LC/MS quantification as described in the SPE procedure section.

TABLE 1

List of pesticides used in this study including their retention times, MRM transitions, optimum collision energies, declustering potentials and entrance potential values. The focusing potential was set to 300 V for all ions.

| Compound | Retention time (min) | MRM transition (m/z) | Collision energy (V) | Declustering potential (V) | Entrance potential (V) |
|---|---|---|---|---|---|
| Methomyl | 4.3 | 163/88 | 15 | 10 | 2 |
| Chloridazon | 7.0 | 222/77 | 50 | 50 | 7 |
| Cyanazine | 10.0 | 241/214 | 20 | 46 | 10 |
| Carbofuran | 11.3 | 222/165 | 20 | 31 | 12 |
| Metsulfuron-methyl | 11.4 | 382/167 | 20 | 56 | 12 |
| Simazine | 12.3 | 202/132 | 25 | 51 | 6 |
| Metazachlor | 15.5 | 278/134 | 25 | 26 | 10 |
| Metalaxyl | 15.9 | 280/220 | 20 | 21 | 6 |
| Atrazine | 16.3 | 216/174 | 25 | 56 | 6 |
| Sebuthylazine (IS)[a] | 20.1 | 230/174 | 30 | 51 | 6 |
| Propazine | 20.3 | 230/146 | 30 | 56 | 6 |
| Parathion-methyl | 20.8 | 264/125 | 25 | 31 | 8 |
| Malathion | 22.0 | 331/127 | 15 | 71 | 11 |
| Azinphos-ethyl | 25.0 | 346/132 | 20 | 31 | 8 |
| Metolachlor | 25.1 | 284/252 | 15 | 36 | 5 |
| Diazinon | 28.6 | 305/153 | 30 | 31 | 6 |

[a]Internal standard

RESULTS AND DISCUSSION

SPE Performance of the GCB Membrane

The ability of the membrane in retaining pesticides available in both a relatively small volume of 1 mL and larger volume of 200 mL, as well as the LC/MS/MS detection limits, were evaluated and shown in Table 2. The breakthrough values listed indicate the fraction of the compounds that were not adsorbed onto the membrane. The obtained recoveries were comparable with previously reported results using GCB cartridges, however by using the membrane format the volume of organic solvents required for both conditioning the membrane and desorption of analytes decreased dramatically and performing SALDI/MS was facilitated.

The effect of SALDI screening on the amount of analyte loss was evaluated by determining the recoveries of the pesticides before and after the SALDI analyses, and as shown in Table 2 it did not result in any substantial differences. Having in mind that the laser aperture area in the MALDI instrument was approximately 0.002 mm$^2$ whereas the area of the membrane was approximately 78.5 mm$^2$, the amount of analyte loss during SALDI screening was negligible.

TABLE 2

Recoveries and breakthroughs were determined after passing 1 mL of a 1.0 µg/mL solution and 200 mL of a 0.05 µg/mL solution through the membrane as well as the recoveries after SALDI analysis. The values are presented as percentages of the initial amounts of each compound present in the samples. LC/MS/MS method LOD values were defined as signal to noise ratios of 3 in analyses of 200 mL solution (0.05 µg/mL) eluted from GCB membrane.

| Compound | 1 mL Breakthrough (RSD %) | Recovery (RSD %) | 200 mL Breakthrough (RSD %) | Recovery before SALDI analysis (RSD %) | Recovery after SALDI analysis (RSD %) | LOD in LC/MS/MS (pg/mL) |
|---|---|---|---|---|---|---|
| Methomyl | 0.3 (88) | 98 (7) | 38 (3) | 62 (3) | 60 (5) | 19 |
| Chloridazon | n.d. | 96 (6) | 19 (7) | 85 (5) | 86 (3) | 81 |
| Cyanazine | n.d. | 109 (14) | 25 (4) | 77 (6) | 75 (7) | 280 |
| Carbofuran | 0.2 (88) | 101 (7) | 31 (12) | 69 (8) | 67 (9) | 5 |
| Metsulfuron-methyl | n.d. | 99 (11) | 20 (5) | 76 (6) | 76 (4) | 4 |
| Simazine | 0.1 (93) | 104 (6) | 22 (3) | 80 (2) | 80 (6) | 9 |
| Metazachlor | 0.1 (98) | 97 (6) | 28 (3) | 77 (4) | 76 (2) | 50 |
| Metalaxyl | 0.1 (87) | 100 (6) | 20 (6) | 79 (8) | 77 (5) | 11 |
| Atrazine | 0.1 (97) | 97 (8) | 21 (2) | 75 (6) | 75 (4) | 10 |
| Propazine | 22 (2) | 74 (9) | 27 (7) | 70 (6) | 71 (5) | 7 |
| Parathion-methyl | n.d. | 78 (6) | n.d. | 76 (8) | 75 (4) | 201 |
| Malathion | n.d. | 90 (8) | 19 (6) | 78 (3) | 78 (2) | 6 |
| Azinphos-ethyl | n.d. | 90 (9) | 15 (3) | 80 (7) | 79 (6) | 125 |
| Metolachlor | n.d. | 95 (8) | 22 (8) | 72 (6) | 72 (3) | 84 |
| Diazinon | 0.1 (75) | 69 (10) | 17 (5) | 57 (8) | 55 (6) | 86 | n.d., not detected

The detection limits for proton, sodium and potassium adducts of pesticides in SALDI analyses are listed in Table 3. Except for metsulfuron-methyl, at least one adduct was detected for each compound. It is feasible to reduce the SALDI detection limits by using a membrane having a smaller surface area; however, one should consider the flow rate and capacity changes.

TABLE 3

LOD values, defined as signal/noise ratios of 3, for SALDI analysis of pesticides retained on the GCB membrane after 200 mL of a 0.05 μg/mL solution has passed through a 78.5 mm² membrane.

| Compound | LOD (ng/mL) | | |
|---|---|---|---|
| | $[M + H]^+$ | $[M + Na]^+$ | $[M + K]^+$ |
| Methomyl | n.d. | 37 | 21 |
| Chloridazon | 10 | 50 | 37 |
| Cyanazine | 21 | 21 | 37 |
| Carbofuran | 8 | 48 | 45 |
| Metsulfuron-methyl | n.d. | n.d. | n.d. |
| Simazine | 4 | n.d. | 30 |
| Metazachlor | 25 | 37 | 30 |
| Metalaxyl | n.d. | 11 | 11 |
| Atrazine | 2 | n.d. | n.d. |
| Propazine | 2 | 12 | 37 |
| Parathion-methyl | 14 | n.d. | 11 |
| Malathion | 25 | 25 | n.d. |
| Azinphos-ethyl | n.d. | 7 | n.d. |
| Metolachlor | 12 | 21 | n.d. |
| Diazinon | 4 | n.d. | 37 | n.d., not detected

The effect of sample flow rate on retention of analytes on the membrane was evaluated. The flow rate of the sample was increased in four steps and the portion of the analytes that passed through the membrane was determined. The membrane was able to retain between 50% of methomyl with a log P=0.6 and 90% of azinphos-ethyl with a log P=3.6 at a flow rate of approximately 50 mL/min, except for parathion-methyl, which was completely retained at all tested flow rates, Table 4a. The high retention of parathion-methyl is most likely attributed to the relatively lower electron density on the benzene ring, which increases the π-π interactions with the electron rich aromatic structure of GCB surface. These observations are in agreement with reported results on the greater than expected retention, based on log P values, of benzene derivatives having electron withdrawing substitutes on a GCB analytical column. The retention profile for all the compounds, except for parathion-methyl, was almost the same in the range of flow rates tested. The fact that parathion-methyl was 100% retained on the membrane even at a flow rate of 50 mL/min indicates that no channels were created as a result of the higher flow rate.

The volume of sample passed through the membrane can also influence the retention behaviour of analytes and this effect was studied by passing increasing volumes of water, up to 1 L, spiked with a constant amount of pesticides through the membrane, Table 4b. As expected, based on log P values of the pesticides, the same profile was observed when increasing the sample volume as with the flow rate. Again no breakthrough was observed for parathion-methyl even when 1 L of sample passed through the membrane. For the pesticides possessing a relatively higher value of log P the breakthrough values were almost constant with increasing sample volumes, but for compounds with lower log P values that have a lower tendency to retain on GCB the breakthrough values increased with increasing the sample volume.

A number of spiked water samples containing different concentrations of the pesticides, at a constant volume, were also passed through the membrane. As shown in Table 4c, the increase in the amount of breakthrough was quite rapid for most of the pesticides going from concentration of 1 μg/mL to 10 μg/mL and after that saturation occurred. The retention mechanisms mentioned above are based on the reversed phase and π-π interactions, and not the anion exchange properties of GCB, since the studied analytes, except for metsulfuron-methyl, were neutral in the working pH.

The ability to use such high flow rates and large sample volumes is a great advantage when dealing with environmental samples which are normally available in large volumes but contain low concentrations of analytes.

TABLE 4a

Membrane retention capacity with different flow rates.

| | Sample flow rate (mL/min) | | | | | | | | | |
|---|---|---|---|---|---|---|---|---|---|---|
| | 7-10 | | 15-19 | | 26-30 | | 35-40 | | 46-50 | |
| | B | RSD | B | RSD | B | RSD | B | RSD | B | RSD |
| Methomyl | 18% | 3% | 25% | 3% | 28% | 3% | 37% | 4% | 48% | 5% |
| Chloridazon | 12% | 2% | 16% | 3% | 18% | 4% | 27% | 5% | 38% | 3% |
| Cyanazin | 10% | 3% | 18% | 3% | 18% | 4% | 26% | 3% | 37% | 3% |
| Carbofuran | 12% | 2% | 18% | 3% | 22% | 4% | 31% | 5% | 36% | 4% |
| Metsulfuron-Methyl | 7% | 2% | 12% | 2% | 13% | 4% | 22% | 3% | 24% | 3% |
| Simazin | 11% | 2% | 18% | 3% | 20% | 5% | 29% | 5% | 42% | 4% |
| Metazachlor | 9% | 2% | 13% | 2% | 16% | 3% | 23% | 3% | 28% | 3% |
| Metalaxyl | 7% | 1% | 12% | 2% | 14% | 3% | 22% | 3% | 26% | 3% |
| Atrazin | 10% | 2% | 17% | 3% | 19% | 3% | 26% | 4% | 37% | 3% |
| Propazin | 22% | 4% | 19% | 3% | 19% | 3% | 26% | 4% | 37% | 3% |
| Parathion-methyl | 0% | 0% | 0% | 0% | 0% | 0% | 0% | 0% | 0% | 0% |
| Malathion | 7% | 1% | 12% | 2% | 14% | 3% | 22% | 2% | 26% | 3% |
| Azinphos-Ethyl | 3% | 1% | 6% | 1% | 6% | 3% | 12% | 1% | 13% | 3% |
| Metolachlor | 6% | 2% | 9% | 1% | 12% | 3% | 19% | 3% | 23% | 3% |
| Diazinon | 5% | 1% | 9% | 1% | 12% | 2% | 17% | 2% | 23% | 2% |

B: breakthrough

TABLE 4b

Membrane retention capacity with different sample volumes.

| | Sample volume (mL) | | | | | | | | | |
|---|---|---|---|---|---|---|---|---|---|---|
| | 100 | | 250 | | 500 | | 750 | | 1000 | |
| | B | RSD | B | RSD | B | RSD | B | RSD | B | RSD |
| Methomyl | 32% | 2% | 43% | 5% | 51% | 3% | 67% | 9% | 82% | 3% |
| Chloridazon | 22% | 2% | 32% | 6% | 37% | 6% | 50% | 8% | 56% | 6% |
| Cyanazin | 23% | 2% | 28% | 6% | 30% | 4% | 35% | 7% | 36% | 3% |
| Carbofuran | 27% | 2% | 35% | 2% | 39% | 4% | 46% | 12% | 60% | 2% |
| Metsulfuron-Methyl | 20% | 2% | 26% | 4% | 28% | 5% | 32% | 3% | 33% | 7% |
| Simazin | 22% | 2% | 27% | 5% | 34% | 5% | 30% | 13% | 36% | 4% |
| Metazachlor | 27% | 2% | 34% | 6% | 36% | 6% | 38% | 8% | 42% | 5% |
| Metalaxyl | 21% | 2% | 26% | 5% | 28% | 5% | 32% | 10% | 36% | 5% |
| Atrazin | 23% | 3% | 29% | 5% | 33% | 6% | 35% | 11% | 37% | 4% |
| Propazin | 25% | 3% | 29% | 5% | 35% | 6% | 36% | 9% | 37% | 2% |
| Parathion-methyl | 0% | 0% | 0% | 0% | 0% | 0% | 0% | 0% | 0% | 0% |
| Malathion | 21% | 4% | 22% | 3% | 24% | 5% | 25% | 7% | 28% | 4% |
| Azinphos-Ethyl | 16% | 3% | 17% | 4% | 19% | 5% | 18% | 7% | 17% | 5% |
| Metolachlor | 23% | 5% | 25% | 4% | 27% | 6% | 30% | 4% | 35% | 7% |
| Diazinon | 12% | 2% | 20% | 4% | 22% | 6% | 22% | 7% | 24% | 3% |

B: breakthrough

TABLE 4c

Membrane retention capacity with different sample concentrations.

| | Sample concentration (µg/mL) | | | | | | | | | |
|---|---|---|---|---|---|---|---|---|---|---|
| | 1 | | 5 | | 10 | | 25 | | 30 | |
| | B | RSD | B | RSD | B | RSD | B | RSD | B | RSD |
| Methomyl | 19% | 3% | 77% | 3% | 97% | 2% | 99% | 3% | 98% | 4% |
| Chloridazon | 0% | 1% | 34% | 1% | 73% | 2% | 88% | 4% | 93% | 2% |
| Cyanazin | 2% | 1% | 17% | 1% | 54% | 2% | 82% | 2% | 83% | 1% |
| Carbofuran | 0% | 4% | 83% | 4% | 96% | 2% | 103% | 3% | 111% | 2% |
| Metsulfuron-Methyl | 4% | 1% | 10% | 1% | 23% | 3% | 36% | 5% | 34% | 3% |
| Simazin | 2% | 1% | 7% | 1% | 18% | 2% | 23% | 3% | 28% | 1% |
| Metazachlor | 5% | 2% | 24% | 2% | 60% | 2% | 78% | 2% | 81% | 1% |
| Metalaxyl | 3% | 2% | 24% | 2% | 67% | 2% | 88% | 2% | 89% | 1% |
| Atrazin | 3% | 2% | 20% | 2% | 56% | 2% | 78% | 3% | 79% | 1% |
| Propazin | 25% | 1% | 23% | 1% | 65% | 2% | 88% | 2% | 108% | 1% |
| Parathion-methyl | 1% | 0% | 1% | 0% | 4% | 1% | 6% | 2% | 8% | 0% |
| Malathion | 5% | 3% | 11% | 3% | 35% | 5% | 34% | 4% | 36% | 1% |
| Azinphos-Ethyl | 1% | 1% | 1% | 1% | 2% | 1% | 2% | 4% | 3% | 0% |
| Metolachlor | 2% | 1% | 7% | 1% | 26% | 2% | 48% | 4% | 50% | 1% |
| Diazinon | 1% | 1% | 3% | 1% | 13% | 2% | 19% | 3% | 25% | 1% |

B: breakthrough

Agricultural Water Analysis

Figure 3:
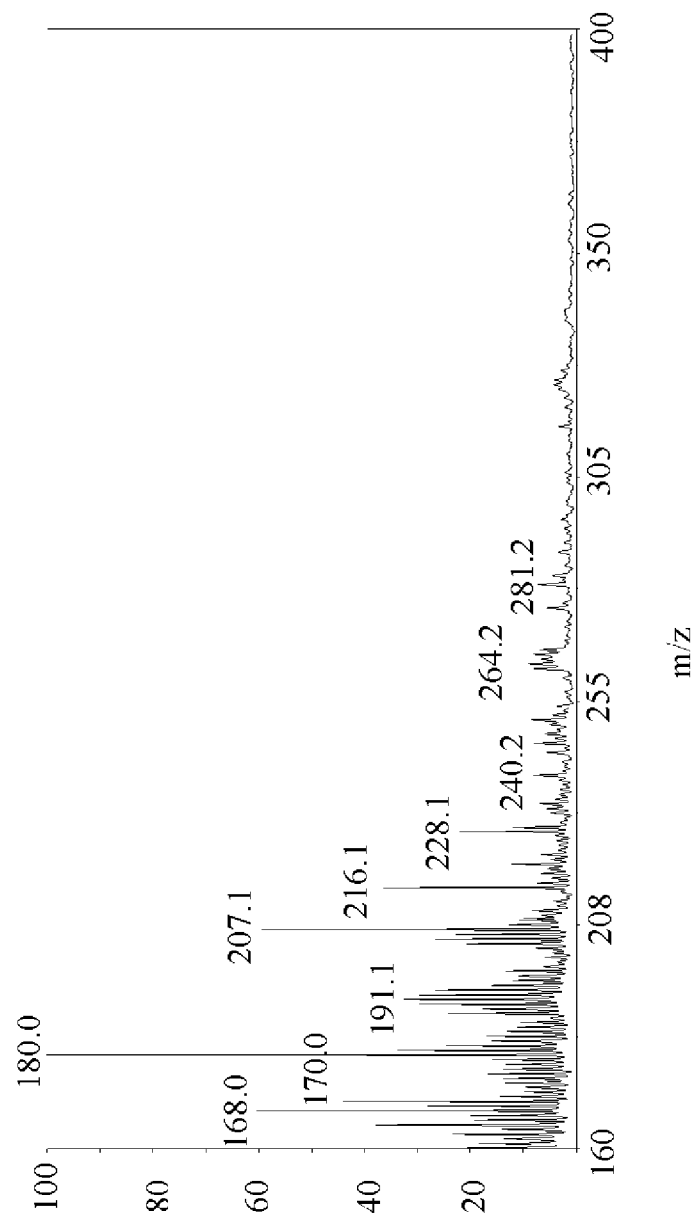
FIG. 3. SALDI Mass spectra using a GCB-loaded PTFE membrane. Representative SALDI-MS spectra from a membrane of the invention.

The applicability of this method for screening and analyzing pesticides in real and complex matrices was investigated in the water collected from the drainage channels of a rice field. High amounts of pesticides are generally used in rice cultivation and their presence in the water of such areas has been previously reported. The water collected for this study was passed through the membrane in duplicate samples and analyzed by LDI. The screening, FIG. 3, revealed ions at 216.1 m/z and 170.0 m/z potentially corresponding to atrazine and one of its major degradation products, atrazine-desethyl-2-hydroxy, and thus further identification and quantification was performed by LC/MS/MS. This analysis confirmed the presence of atrazine with a concentration of 110.7±0.3 µg/L as well as two other pesticides, simazine 5.7±0.1 µg/L and diazinone 14.0±0.2 µg/L, which did not appear in the SALDI analysis due to their low concentrations. The presence of atrazine-desethyl-2-hydroxy was confirmed by comparing its retention time and fragmentation pattern in the sample with the corresponding standard.

The invention claimed is:

1. A particle loaded membrane, which is porous such that a liquid may pass through it comprising a support and particles attached to the support, for solid-phase extraction of an analyte from a sample to be analysed, characterized by that:
   i) the particles comprise graphitized carbon black (GCB) or derivates thereof; and
   ii) the support is suitable for surface-assisted laser desorption ionisation mass spectrometry (SALDI-MS) of analytes extracted on the particles.

2. The particle loaded membrane of claim 1, further characterized by that the support is essentially inert with regard to binding of the organic analyte.

3. The particle loaded membrane of claim 1, further characterized by that the support comprises PTFE, cellulose, polyether sulfonate, Nylon or glassfiber.

4. The particle loaded membrane of claim 3, further characterized by that the support consists of PTFE, cellulose, polyether sulfonate, Nylon or glassfiber.

5. The particle loaded membrane of claim 4, further characterized by that the support consists of PTFE.

6. The particle loaded membrane of claim 1, further characterized by that the support is about 0.01-5 mm in thickness.

7. The particle loaded membrane of claim 1, further characterized by that the GCB particles have a size in the range of about 37.5-120 μm.

8. The particle loaded membrane of claim 1, further characterized by that the GCB content of the membrane is about 90% by weight.

9. The particle loaded membrane of claim 1, further characterized by that the GCB particles are type 1 or type 4 GCB particles.

10. A filter device suitable for solid phase extraction of an organic analyte from a sample by filtration, characterized by that a membrane according to claim 1 is arranged into the filter device such that the analyte is solid-phase extracted onto the membrane.

11. The filter device of claim 10, further characterized by that the device is a filter plate device.

12. The filter device of claim 11, further characterized by that the device is a filter plate device having dimensions that conform to standards ANSI/SB S 1-2004, ANSI/SBS 2-2004, ANSI/SBS 3-2004 and/or ANSI/SB S 4-2004.

13. A method of performing SALDI-MS-analysis of an analyte in a sample, characterized by that it comprises the steps of:
   i) performing solid phase extraction of the analyte onto a membrane according to claim 1; and
   ii) performing SALDI-MS-analysis of the extracted analyte.

14. The method of claim 13 characterized by that it further comprises the step of: iii) desorbing the analytes and performing quantitative liquid chromatography/mass spectrometry (LC/MS) on the analytes.

15. The particle loaded membrane of claim 6, wherein the support is about 0.5 mm in thickness.

16. A method of performing SALDI-MS-analysis of an analyte in a sample, characterized by that it comprises the steps of:
   i) performing solid phase extraction of the analyte onto a device according to claim 10; and
   ii) performing SALDI-MS-analysis of the extracted analyte.

* * * * *